United States Patent [19]

Burke

[11] Patent Number: 5,088,983
[45] Date of Patent: Feb. 18, 1992

[54] PRESSURE REGULATOR FOR IMPLANTABLE PUMP

[75] Inventor: Paul Burke, Woonsocket, R.I.

[73] Assignee: Infusaid, Inc., Norwood, Mass.

[21] Appl. No.: 724,032

[22] Filed: Jul. 1, 1991

Related U.S. Application Data

[62] Division of Ser. No. 412,376, Sep. 26, 1989.

[51] Int. Cl.$^5$ ............................................. A61M 37/00
[52] U.S. Cl. ............................ 604/141; 128/DIG. 12; 604/246; 604/891.1
[58] Field of Search ............................ 128/DIG. 12; 604/65–67, 93, 131, 140–141, 246–247, 890.1, 891.1; 417/472

[56] References Cited

U.S. PATENT DOCUMENTS

| | | | |
|---|---|---|---|
| 4,258,711 | 3/1981 | Tucker et al. | 128/DIG. 12 X |
| 4,299,220 | 11/1981 | Dorman | 128/260 |
| 4,557,726 | 12/1985 | Reinicke | 604/67 |
| 4,718,893 | 1/1988 | Dorman et al. | 604/67 |
| 4,838,887 | 6/1989 | Idriss | 604/891.1 |
| 4,902,278 | 2/1990 | Maget et al. | 604/132 |
| 4,931,050 | 6/1990 | Idriss | 604/891.1 |

Primary Examiner—C. Fred Rosenbaum
Assistant Examiner—Corrine Maglione
Attorney, Agent, or Firm—Sughrue, Mion, Zinn, Macpeak & Seas

[57] ABSTRACT

An implantable pump system employing a flow regulator isolates the regulator sensing chamber from the path of drug flow. This is accomplished by establishing either an independent sensing chamber in the regulator or coupling it to the propellant chamber of the pump. Additionally, a downstream restrictor may be used to provide an additional pressure drop between the regulator and the outlet catheter.

16 Claims, 1 Drawing Sheet

PRESSURE REGULATOR FOR IMPLANTABLE PUMP

This is a divisional of application Ser. No. 07/412,376 filed Sept. 26, 1989.

FIELD OF THE INVENTION

This invention is directed to a system for accurately controlling a flow rate of a drug from an implantable drug delivery device and maintaining in-vivo a higher degree of safety. Devices of this type have reached the point of commercial utilization as typified by the Infusaid models 100 and 400 devices. In the literature, such implantable infusion pumps are described in U.S. Pat. No. 3,731,681. Such devices are implanted in a living body to deliver a drug at a very slow flow rate over a long period of time. They are refilled subcutaneously.

PRIOR ART

U.S. Pat. No. 3,731,681 describes an implantable infusion pump employing a liquid/vapor to provide a constant pressure for a drug flowing through a capillary tube in order to maintain a constant flow rate. This technique of flow control, while simple and reliable, is sensitive to outside variables such as changes in temperature and atmospheric pressure. Because the temperature of the body in which the device is implanted remains relatively constant, the vapor pressure also stays relatively constant. Similarly, where a patient remains in one local region the air pressure is essentially constant. However, there are conditions in which both body temperature and atmospheric pressure may have significant changes. For example, if the patient has a fever or works in an unusually cold environment the temperature of the implanted device may change by several degrees. This may result in a 25% increase in pressure as a result of such a temperature change which results in a variation of the flow rate. For example, a fever in the range of 104° F. can result in such a change.

Another example of a pressure shift which results in a change of drug flow rate is a variation in atmospheric pressure. The most common atmospheric change occurs during an airplane flight wherein the cabin is maintained at a pressure corresponding to an altitude of approximately 6,500 feet above sea level. At sea level, such an implanted device would have an internal pressure of approximately 8.2 psig. At 6,500 feet the decrease in atmospheric pressure would result in a drug flow rate increase of approximately 40% over the sea level setting. A modification of the drug concentration to adjust dosage is possible, but represents a serious inconvenience and hardship to the patient.

To compensate for variations in temperature and pressure, U.S. Pat. No. 4,299,220 relates to an improved implantable pump which uses a regulator to compensate for variations in temperature and pressure. The regulating device comprises a pair of chambers separated by a flexible diaphragm. The first chamber is in fluid contact with the reservoir of the pump and has an outlet allowing the reservoir fluid to flow into a restrictor. This restrictor flows into the other chamber and communicates with the pump outlet via a centrally located regulating seal. The relationship of the regulator seal to the flexible diaphragm permits the regulator to maintain a constant pressure drop across the restrictor despite reservoir or outlet pressure variations.

While the configuration disclosed in the '220 patent offers pressure regulation, the flow paths have potentially undesirable failure modes. For example, since the regulator depends on the drug fluid to supply the regulator sensing pressure, a diaphragm failure, such as a hole in the membrane, would allow the drug to bypass the regulator's restrictor resulting in an undesirable increase in flow rate. Another potential problem is a failure of the regulator seal, that is, a seal leak or physical dislocation of the seal relative to the seat. This would result in a flow rate increase due to the lack of seal restriction. Given that safety of such implantable devices is a standing criteria, a need exists in the art to eliminate the potential failure modes when utilizing a flow rate regulator.

SUMMARY OF THE INVENTION

Given the deficiencies of the prior art, it is an object of this invention to provide for an improved pressurized flow regulator used in an implantable drug system.

Yet another object of this invention is to provide a regulating device that eliminates the failure modes which are inherent in prior art systems.

These and other objects of this invention are accomplished by utilizing flow regulators that have the first chamber pressurized with the same liquid/vapor propellant drug reservoir. Additionally, the use of a downstream restrictor provides a fail-safe such that a failure in the regulator seal will not result in excessive pump flow rate to the drug delivery site.

These and other aspects of this invention will be defined by referring to the attached drawing and the description of the preferred embodiment which follow.

DESCRIPTION OF THE PREFERRED EMBODIMENTS

Figure 1:
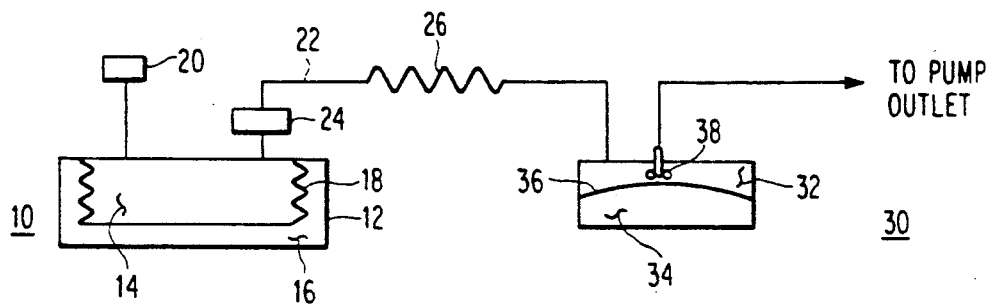
FIG. 1 is a first embodiment of an implantable drug system in accordance with this invention.

Referring now to FIG. 1, a first preferred embodiment of this invention is depicted. In this embodiment, the drug delivery device comprises an implantable infusion pump 10 comprising a housing 12 divided into two chambers, a drug reservoir chamber 14 and a propellant chamber 16. A bellows diaphragm 18 is used to divide the interior into the chambers 14 and 16. A refill septum 20 provides fluid communication to allow for subcutaneous refilling of the drug reservoir 14 without explanting the device. The septum comprises a penetrable resilient stopper. The propellant chamber 16 contains a liquid having a vapor pressure which, under conditions of normal body pressure exerts a pressure on the bellows to force a drug contained in the drug reservoir 14 out through conduit 22. A bacteria filter 24 is placed in-line between the drug reservoir 14 and the outlet conduit 22.

In accordance with this embodiment of the invention, flow restrictor 26 is placed on the outlet line 22 to provide a pressure drop.

A drug at the delivered pressure is then input into a flow regulating device 30. In accordance with this invention this device comprises a regulator chamber 32 and the sensing chamber 34 divided by a thin flexible diaphragm 36. A regulator seal 38 is employed to define a stop for the flexible diaphragm 36. The regulator seal 38 and the flexible diaphragm 36 are worked in the manner as described in U.S. Pat. No. 4,299,220. The disclosure of that patent is incorporated herein by reference to the extent that it discloses the construction of the diaphragm 36 and the regulator seal 38 which are used in accordance with this invention.

As illustrated in FIG. 1, a principal difference between this embodiment of the invention and the system illustrated in U.S. Pat. No. 4,299,220 is that in the prior art device, the regulator 30 would be in fluid contact with the implantable infusion pump drug reservoir to maintain a constant flow rate by compensating for changes in the pump reservoir or outlet pressures. Thus, the prior art uses a diaphragm-to-seal technology which has the sensing chamber in fluid contact with the reservoir. However, in accordance with this invention, as illustrated in FIG. 1, the sensing chamber 34 is sealed from the fluid flow path. It is filled with the same 2-phase fluid as in the pump propellant chamber 16. Thus, the sensing chamber 34 contains the same vapor pressure as the pump propellant chamber 16. It thus parallels pressure fluctuations experienced by the propellant chamber 16.

If the internal pressure in the drug reservoir 14 is $P_1$ and the pressure inside regulator chamber 32 is $P_2$, then the pressure differential across the restrictor 26 is $P_1 - P_2$ and the pressure differential across the flexible diaphragm is $P_1 - P_2$.

One limitation of this type of regulator is that it is not capable of regulating additional forces exerted on the drug reservoir other than the propellant pressure, for example, the bellows spring force. While this design limitation must be considered in determining the overall acceptability of the system, it does not outweigh the solution to a major disadvantage by making the regulator a fail-safe component. Thus, the fact that the regulator contains an independent pressure source allows a sensing chamber 34 to operate without communicating with the drug reservoir 14. This eliminates the possibility of drug solution bypassing the regulator due to a diaphragm hermeticity failure.

The regulator of FIG. 1 could be contained within the housing for the implantable pump component, that is, generally within the container 12 or alternatively as an independent component added to the outlet 22 of the pump system.

Figure 2:
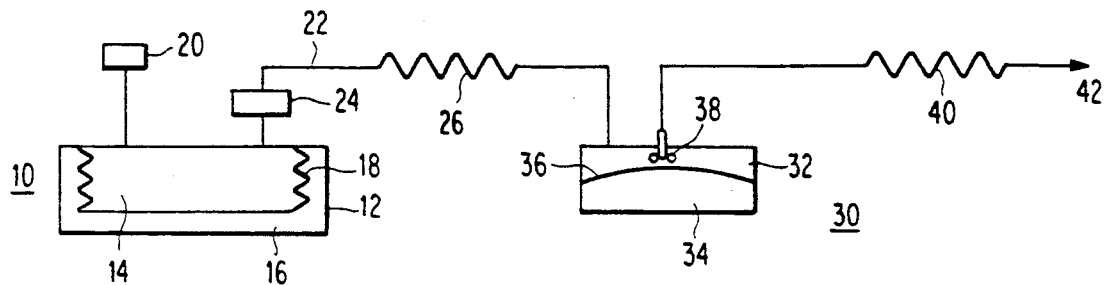
FIG. 2 is a second embodiment of this invention utilizing a downstream restrictor element in accordance with this invention.

Referring now to FIG. 2, a second embodiment of this invention is depicted. In FIG. 2, those elements which have been described in the first embodiment have been given common numbering.

In the FIG. 2 embodiment, a second restrictor 40 is employed to establish a pressure drop across the regulator 30. Thus, a first restrictor 26 establishes a pressure drop between the pump 10 and the regulator 30 while the downstream restrictor 40 establishes a pressure drop between the catheter 42 at the outlet point and the flow regulating device 30. The restrictor 26 has a low restrictive value, and is used to establish the pressure drop across the regulating chambers 32 and 34. However, the majority of the pump's flow restriction is established by the restrictor 40 located downstream of the regulator seal. With the majority of the restriction located downstream, a failure in the regulator seal 38 will not result in excessive pump flow rates, that is, increases possible if only a single flow restrictor were employed.

Figure 3:
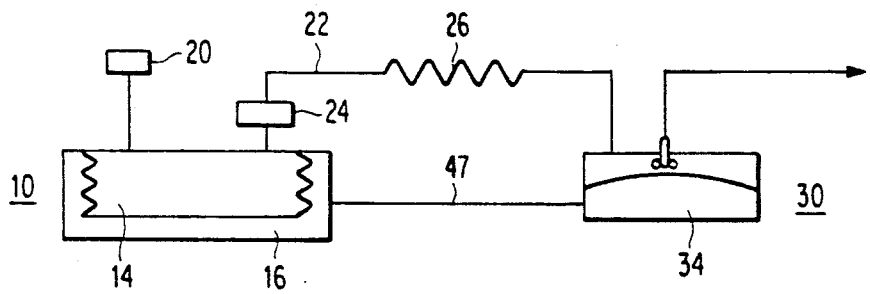
FIG. 3 is a third embodiment of this invention which couples the propellant and sensing chambers together in accordance with this invention.

Referring now to FIG. 3, a third embodiment of this invention is depicted. In the FIG. 3 embodiment, the propellant chamber 16 is physically coupled to the sensing chamber 34 in the regulating device 30 via a line 44. The embodiment of FIG. 3 departs from that of FIG. 1 in that, instead of having the sensing chamber 34 provided with an independent source of propellant fluid, the same material, such as a Freon 2-phase fluid is used in common in chamber 16 and chamber 34.

Figure 4:
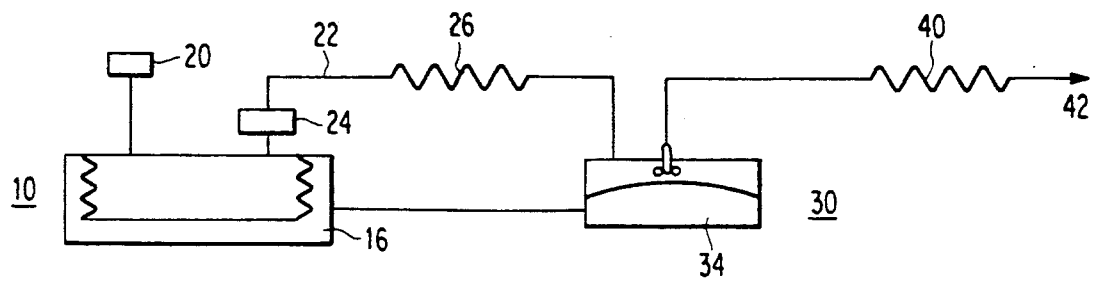
FIG. 4 is a fourth embodiment of this invention utilizing the combination of a downstream restrictor and the propellant and sensing chambers coupled together.

FIG. 4 represents a fourth embodiment that is a combination of FIGS. 2 and 3. In FIG. 4 the combination of upstream restrictor 26 and downstream restrictor 40 is used to provide two differential pressure drops respectively between the pump 10 and the regulator 30 and the outlet catheter 42. Additionally, the common tieing of the propellant chamber 16 and the sensing chamber 34 utilizing the line 44 is accomplished so that those two chambers are in direct fluid communication with each other.

As is apparent, in each of these embodiments regulator sensing is not dependent on the flow of drug from the outlet 22. Rather, in each, the sensing chamber in the regulator is established with either an independent source of propellant to establish a base line regulating pressure or, is coupled in direct fluid communication with the propellant chamber in the drug dispensing device. Moreover, by the use of a downstream restrictor a failure in the regulator seal will not cause a catastrophic failure since the restrictor will still establish necessary pressure drop.

It is apparent that modifications of this invention may be practiced without departing from the essential scope thereof.

I claim:

1. An implantable drug delivery system comprising:
   a pressure actuated drug dispensing device having a sealed body, said sealed body having a flexible drug reservoir containing a fluid, an outlet from said flexible drug reservoir and a propellant chamber in said sealed body pressurized to a pressure to urge said fluid from said flexible drug reservoir into said outlet, and
   a flow regulating device having a regulator chamber and a sensing chamber, said regulator chamber and said sensing chamber separated and maintained in isolation from each other by a flexible diaphragm, said outlet supplying said fluid into said regulator chamber, an outlet catheter coupling said regulator chamber to a drug delivery site and, means not using said fluid to establish a reference pressure in said sensing chamber that is substantially equal to said pressure in said propellant chamber comprising a fluid coupling between said propellant chamber and said sensing chamber.

2. The system of claim 1 wherein said means to establish a reference pressure comprises a source of propellant in said sensing chamber that is the same as in the propellant chamber of said drug dispensing device.

3. The system of claim 2 further comprising a flow restrictor element placed in said outlet catheter.

4. The system of claim 1 further comprising a penetrable septum coupled to said drug reservoir for refilling said fluid.

5. The system of claim 1 further comprising a bacteria filter in said outlet and flow restrictor disposed in said outlet upstream of said regulator chamber.

6. The system of claim 1 further comprising a regulator seal in said regulating chamber of said flow regulating device, said regulator seal positioned relative to said diaphragm to vary the flow of fluid to said outlet catheter.

7. The system of claim 6 wherein said flexible drug reservoir comprises a bellows disposed in said sealed body to define said drug reservoir.

8. The system of claim 6 wherein said flexible diaphragm is biased to deflect in the direction said regulator seal.

9. An implantable drug delivery system comprising:
a sealed body having a flexible drug reservoir and a separate propellant chamber therein, a fluid in said drug reservoir, an outlet coupled to said drug reservoir, a flow regulating device physically coupled to said sealed body, said flow regulating device comprising a regulating chamber in fluid contact with said drug reservoir, a flexible diaphragm in said flow regulating device, a sensing chamber in said flow regulating device in fluid separation from said regulating chamber, means separate from said fluid in said drug reservoir and coupled to said propellant chamber to define a reference pressure in said sensing chamber substantially replicating the pressure in said propellant chamber such that said flexible diaphragm moves in response to variations in flow rate in said outlet to regulate the pressure in said regulating chamber and an outlet catheter coupled to said regulating chamber.

10. The system of claim 9 wherein said means to establish a reference pressure comprises a source of propellant in said sensing chamber that is the same as in the propellant chamber of said drug dispensing device.

11. The system of claim 10 further comprising a restrictor element placed in said outlet catheter.

12. The system of claim 9 further comprising a penetrable septum coupled to said drug reservoir for refilling said fluid.

13. The system of claim 9 further comprising a bacteria filter in said outlet and flow restrictor disposed in said outlet upstream of said regulator chamber.

14. The system of claim 9 further comprising a regulator seal in said regulating chamber of said flow regulating device, said regulator seal positioned relative to said diaphragm to vary the flow of fluid to said outlet catheter.

15. The system of claim 14 wherein said flexible drug reservoir comprises a bellows disposed in said sealed body to define said drug reservoir.

16. The system of claim 14 wherein said flexible diaphragm is biased to deflect in the direction of said regulator seal.

* * * * *